United States Patent
Lin et al.

(10) Patent No.: US 9,778,183 B2
(45) Date of Patent: Oct. 3, 2017

(54) SENSING CHIP

(71) Applicant: INDUSTRIAL TECHNOLOGY RESEARCH INSTITUTE, Hsinchu (TW)

(72) Inventors: Ding-Zheng Lin, Taipei (TW); Yi-Ping Chen, Kaohsiung (TW); Ping-Chen Chen, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 55 days.

(21) Appl. No.: 14/831,248

(22) Filed: Aug. 20, 2015

(65) Prior Publication Data

US 2017/0052114 A1    Feb. 23, 2017

(51) Int. Cl.
| | |
|---|---|
| *G01N 21/55* | (2014.01) |
| *G01N 21/65* | (2006.01) |
| *G01N 21/552* | (2014.01) |
| *B82Y 20/00* | (2011.01) |

(52) U.S. Cl.
CPC .......... *G01N 21/554* (2013.01); *B82Y 20/00* (2013.01); *G01N 21/658* (2013.01); *Y10S 977/954* (2013.01)

(58) Field of Classification Search
CPC ................. G01N 21/554; G01N 21/658
See application file for complete search history.

(56) References Cited

U.S. PATENT DOCUMENTS

| | | |
|---|---|---|
| 6,278,231 B1 | 8/2001 | Iwasaki et al. |
| 6,838,297 B2 | 1/2005 | Iwasaki et al. |
| 6,870,237 B1 | 3/2005 | Lin et al. |
| 7,126,975 B2 | 10/2006 | Iwasaki et al. |
| 7,425,740 B2 | 9/2008 | Liu et al. |
| 7,636,214 B2 | 12/2009 | Imada et al. |
| 7,732,015 B2 | 6/2010 | Nomura et al. |
| 7,898,667 B2 | 3/2011 | Yamada et al. |
| 8,023,114 B2 * | 9/2011 | Yamamichi .......... G01N 21/554 356/445 |
| 8,279,436 B2 | 10/2012 | Lin et al. |

(Continued)

FOREIGN PATENT DOCUMENTS

| | | |
|---|---|---|
| CN | 201408192 Y | 2/2010 |
| CN | 104237195 A | 12/2014 |

(Continued)

OTHER PUBLICATIONS

Taiwanese Office Action and Search Report, dated Feb. 15, 2016, for Taiwanese Application No. 103119848.

(Continued)

*Primary Examiner* — Shawn Decenzo
(74) *Attorney, Agent, or Firm* — Birch, Stewart, Kolasch & Birch, LLP (57) ABSTRACT

A sensing chip is provided, which includes a substrate and a plurality of nano structures periodically arranged on the substrate, wherein each of the nano structures includes a bottom metal layer disposed on the substrate, a middle dielectric layer disposed on the bottom metal layer, and a top metal layer disposed on the middle dielectric layer. The bottom metal layer has an area that is larger than that of the top metal layer.

14 Claims, 12 Drawing Sheets

(56) References Cited

U.S. PATENT DOCUMENTS

| | | | |
|---|---|---|---|
| 8,958,070 B2* | 2/2015 | Wang | G01N 21/658 356/432 |
| 9,019,494 B2 | 4/2015 | Lin et al. | |
| 2001/0019565 A1 | 9/2001 | Iwasaki et al. | |
| 2001/0028872 A1 | 10/2001 | Iwasaki et al. | |
| 2004/0218651 A1 | 11/2004 | Iwasaki et al. | |
| 2006/0054506 A1 | 3/2006 | Natan et al. | |
| 2006/0087758 A1 | 4/2006 | Imada et al. | |
| 2007/0080387 A1 | 4/2007 | Liu et al. | |
| 2007/0235342 A1 | 10/2007 | Matsuo et al. | |
| 2007/0240757 A1 | 10/2007 | Ren et al. | |
| 2008/0085364 A1 | 4/2008 | Nomura et al. | |
| 2009/0268205 A1 | 10/2009 | Naya | |
| 2009/0278233 A1 | 11/2009 | Pinnington et al. | |
| 2010/0206380 A1 | 8/2010 | Lindquist et al. | |
| 2011/0001117 A1 | 1/2011 | Lieber et al. | |
| 2011/0117726 A1 | 5/2011 | Pinnington et al. | |
| 2011/0201527 A1 | 8/2011 | Lin et al. | |
| 2011/0267607 A1* | 11/2011 | Hu | G01N 21/658 356/301 |
| 2012/0104346 A1 | 5/2012 | Yi et al. | |
| 2012/0327417 A1 | 12/2012 | Amako et al. | |
| 2013/0038870 A1* | 2/2013 | Lin | G01N 21/658 356/301 |
| 2013/0092211 A1 | 4/2013 | Collin et al. | |
| 2014/0362373 A1 | 12/2014 | Lin et al. | |

FOREIGN PATENT DOCUMENTS

| | | |
|---|---|---|
| JP | 2008-2943 A | 1/2008 |
| JP | 2013-7614 A | 1/2013 |
| TW | 200715477 | 4/2007 |
| TW | I310593 B | 6/2009 |
| TW | 201329436 A1 | 7/2013 |
| TW | I410621 B | 10/2013 |
| TW | I481858 B | 4/2015 |
| TW | I485388 B | 5/2015 |
| WO | WO 01/39285 A3 | 5/2001 |

OTHER PUBLICATIONS

Andrea Cattoni et al., "$\lambda 3/1000$ Plasmonic Nanocavities for Biosensing Fabricated by Soft UV Nanoimprint Lithography", 2011 American Chemical Society, NANO Letters Nov. 2011, pp. 3557-3563.

TW Office Action 103119848 dated Sep. 2, 2015, pp. 1-7.

W. Paige Hall et al., "LSPR Biosensor Signal Enhancement Using Nanoparticle-Antibody Conjugates", 2011 American Chemical Society, J. Phys. Chem., C2011, 115, pp. 1410-1414.

Feuz et al., "Improving the Limit of Detection of Nanoscale Sensors by Directed Binding to High-Sensitivity Areas", ACS NANO, 2010, vol. 4, No. 4, pp. 2167-2177.

Hao et al., "Symmetry Breaking in Plasmonic Nanocavities: Subradiant LSPR Sensing and a Tunable Fano Resonance", American Chemical Society, NANO Letters, 2008, vol. 8, No. 11, pp. 3983-3988.

Kubo et al.,"Au Double Nanopillars with Nanogap for Plasmonic Sensor", American Chemical Society, NANO Letter, 2011, vol. 11, pp. 8-15.

Lassiter et al., "Fano Resonances in Plasmonic Nanoclusters: Geometrical and Chemical Tunability", American Chemical Society, NANO Letters, 2010, vol. 10, pp. 3184-3189.

Liu et al., "High Sensitivity Localized Surface Plasmon Resonance Sensing Using a Double Split NanoRing Cavity", The Journal of Physical Chemistry, Nov. 2011, vol. 115, pp. 24469-24477.

Massiot et al., "Multi-resonant absorption in ultra-thin silicon solar cells with metallic nanowires", Optics Express, May 2013, vol. 21, No. S3, pp. A372-A381.

* cited by examiner

SENSING CHIP

TECHNICAL FIELD

The technical field relates to a sensing chip, and in particular it relates to a method of forming a nano structure of a sensing chip.

BACKGROUND

The enzyme-linked immunosorbent assay (ELISA) is the main method used in medical inspections, such as those for food safety or cancer screening. Conventional ELISA technology has high sensitivity, but it also has other shortcomings such as ELISA kits being expensive, time-consuming to use, and requiring complicated inspection steps. Moreover, the analyte should be tagged by a bio-tag (such as fluorescent molecules) or enzyme for a color reaction, but the fluorescent molecules interfere with the actions of target molecules. Most of the fluorescent molecules have problems such as photobleaching or blinking, so that ELISA errors occur easily when detecting an analyte of low concentration.

Chips of localized surface plasmon resonance (LSPR) can be free of any labeling with a fast inspection effect, in which the surface plasmon resonance spectra of a metal nano structure are utilized. Because the LSPR is sensitive to a refractive index change of a metal-dielectric interface, the chip can be used to detect a trace amount of an analyte (e.g. antigen, antibody, DNA or cell) absorbed on a surface of the nano structure with a distance of tens of nanometers therebetween. In an LSPR chip, the change of the surface plasmon resonance spectra of the metal nano structure to the surrounding refractive index variation ($\Delta\lambda/\Delta n$) is critical for detection sensitivity. In addition, the narrower full width at half maximum (FWHW) of the resonance spectra means a higher spectra resolution and a better detection sensitivity. The figure of merit (FOM) of the chip can be defined as Formula 1:

$$\text{Figure of Merit } (FoM) = \frac{\frac{\Delta\lambda}{\Delta n}(nm/RIU)}{FWHM(nm)} \quad \text{(Formula 1)}$$

Compared to conventional ELISA technology, the LSPR technology has several advantages such as being free of fluorescence labeling, reducing inspection steps and time, and no steric effect of conjugated secondary antibody (containing fluorescent molecules). However, the LSPR chip has a lower sensitivity than the ELISA method due to a wider FWHW of the general localized plasmon resonance spectrum. In addition, whether or not the analyte is close to hot spots (effective sensing area) of the nano structure is also critical for producing an effective spectra shift.

Accordingly, a novel LSPR structure is called for to improve the detection sensitivity and spectra resolution (e.g. reducing FWHW of resonance wavelength) to detect an analyte of a lower concentration.

SUMMARY

One embodiment of the disclosure provides a sensing chip, comprising: a substrate; and a plurality of nano structures periodically arranged on the substrate, wherein each of the nano structures includes a bottom metal layer disposed on the substrate, a middle dielectric layer disposed on the bottom metal layer, and a top metal layer disposed on the middle dielectric layer, wherein the bottom metal layer has an area that is larger than that of the top metal layer.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are shown schematically in order to simplify the drawing.

Figure 1A:
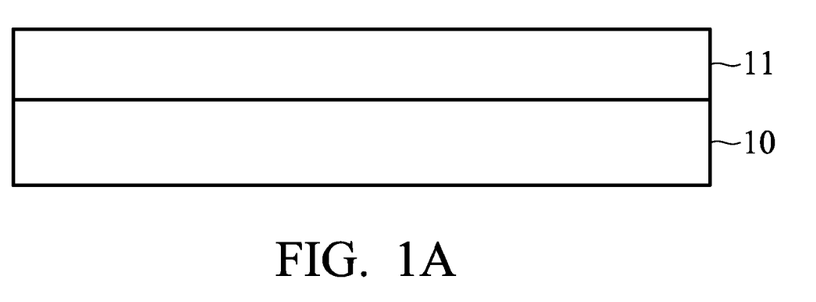
FIGS. 1A to 1D show cross-sectional views of intermediate stages in a process of manufacturing a sensing chip in one embodiment of the disclosure.

FIGS. 1A to 1D show cross-sectional views of intermediate stages in a process of manufacturing a sensing chip 1 in one embodiment of the disclosure. As shown in FIG. 1A, a substrate 10 is provided, and a photoresist layer 11 was then formed on the substrate 10. The substrate 10 can be a dielectric layer such as polyethylene terephthalate (PET), poly methyl methacrylate (PMMA), silica ($SiO_2$), alumina (sapphire), glass, or another common dielectric material. The substrate 10 has refractive index $n_s$ of 1.2 to 4.5, which is related to a plasmon resonance wavelength of the nano structure 20 as described below. A substrate 10 with overly high refractive index $n_s$ may make the plasmon resonance wavelength red-shift to an inferred (IR) range, thereby increasing the cost of related spectroscopic equipment.

Figure 1B:
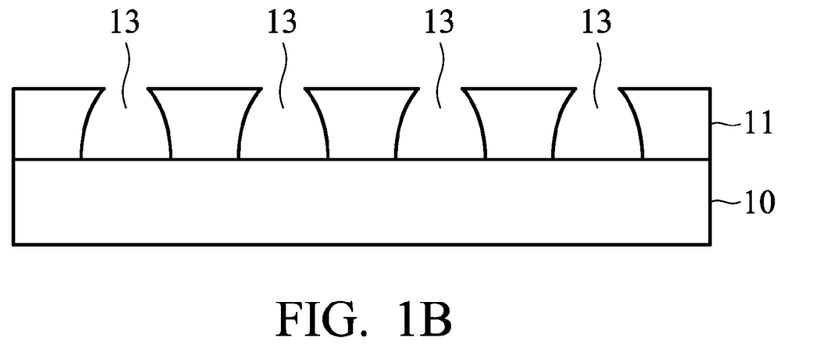

As shown in FIG. 1B, the photoresist layer 11 is then selectively exposed by a photomask, and the patterned photoresist layer 11 has periodically arranged openings 13. The photoresist layer 11 can be positive photoresist or negative photoresist, which can be patterned by corresponding photomasks. The opening 13 of the patterned photoresist layer 11 may have a narrow top and wide bottom shape (undercut) by adjusting the lithography and etching conditions, wherein sidewalls of the openings 13 can be curved (see FIG. 1B) or straight (not shown).

Figure 1C:
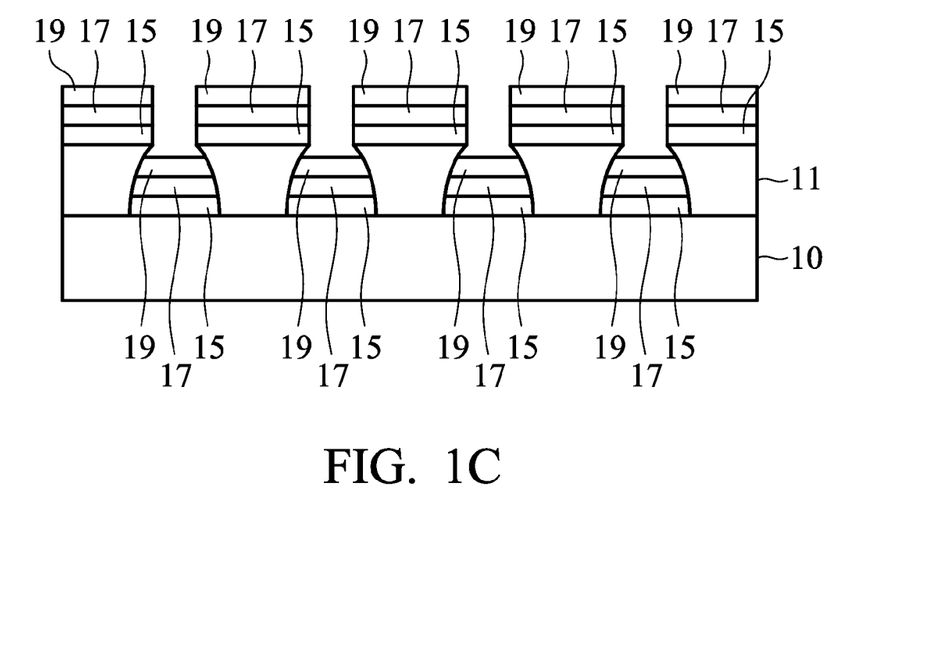

As shown in FIG. 1C, a bottom metal layer 15, a middle dielectric layer 17, and a top metal layer 19 were then sequentially deposited in the openings 13 and on the photoresist layer 11. The bottom metal layer 15 can be gold, silver, aluminum, chromium, copper, titanium, or an alloy thereof. In one embodiment, the bottom metal layer 15 and the top metal layer 19 can be composed of the same material. In one embodiment, the bottom metal layer 15 has a thickness of mm to 40 nm. An overly thin bottom metal layer 15 cannot be easily formed to have a uniform thickness. An overly thick bottom metal layer 15 cannot be formed by a lift-off method. The middle dielectric layer 17 can be alumina, silica, silicon nitride, or a combination thereof. In one embodiment, the middle dielectric layer 17 has a thickness of 1 nm to 10 nm. An overly thin middle dielectric layer 17 cannot be easily formed to have a uniform thickness. An overly thick middle dielectric layer 17 may cause a poor coupling effect of the surface plasmon resonance mode between the bottom metal layer and the top metal layer, thereby reducing the spectra adjustability of the nano structure. Moreover, because mode 1 is more sensitive than mode 2 (see FIG. 8), when the separation of two modes is too small, the overlap of spectra during measurement will reduce the dynamic range of this sensor chip. The top metal layer 19 can be gold, silver, aluminum, chromium, copper, titanium, or an alloy thereof. In one embodiment, the top metal layer 15 has a thickness of 2 nm to 40 nm. An overly thin top metal layer 19 cannot be easily formed to have a uniform thickness. An overly thick top metal layer 19 cannot be formed by a lift-off method.

Subsequently, the photoresist layer 11 and materials deposited thereon are then stripped, and the bottom metal layer 15, the middle dielectric layer 17, and the top metal layer 19 in the openings 13 are kept to stack as nano structures 20. In one embodiment, the nano structures 20 have a width of 50 nm to 1000 nm. An overly small nano structure width makes it hard to control the uniformity of the size of the structure. An overly wide nano structure width make the plasmon resonance wavelength red-shift to the IR range, thereby increasing the cost of related spectroscopic equipment. In one embodiment, the width of the nano structures 20 is greater than or equal to the height of the nano structures 20 (equal to the total thickness of the bottom metal layer 15, the middle dielectric layer 17, and the top metal layer 19). If the height of the nano structures 20 is greater than the width of the nano structures 20, the overly high aspect ratio of height/width will result in a difficult process.

Figure 2A:
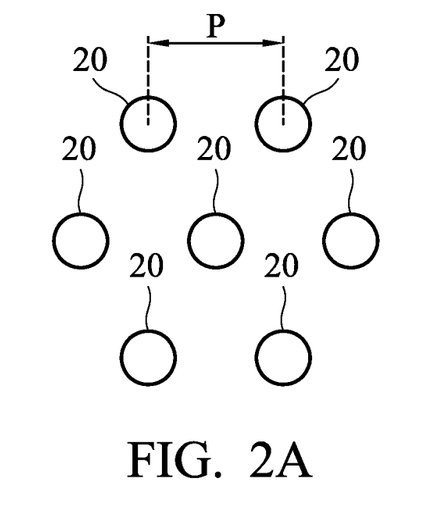
FIGS. 2A to 2B show top-views of periodically arranged nano structures in embodiments of the disclosure.
Figure 2B:
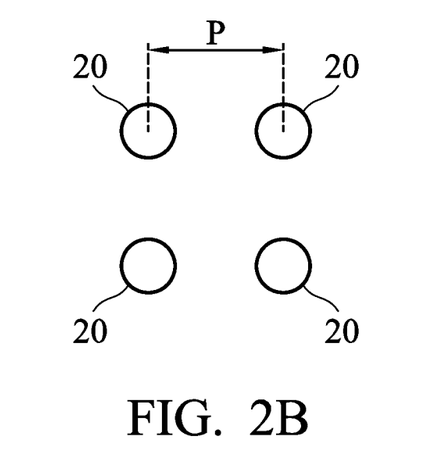
Figure 3A:
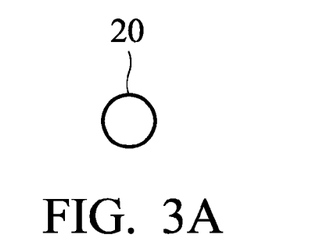
FIGS. 3A to 3C show top-views of the nano structure units in embodiments of the disclosure.
Figure 3B:
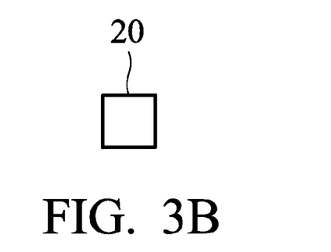
Figure 3C:
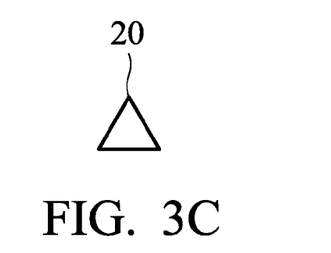

While the openings 13 of the photoresist layer 11 are periodically arranged, the corresponding nano structures 20 are also periodically arranged in a period P of 100 nm to 2000 nm. An overly large period P makes the corresponding Rayleigh ananomy locate at the IR range. An overly small period P makes the corresponding Rayleigh ananomy locate at an ultraviolet (UV) range. Moreover, the overly small period P is not easily manufactured. The nano structures 20 can be arranged in a hexagonal manner (FIG. 2A), a rectangle manner (FIG. 2B), or another suitable manner from top-view. In addition, the nano structure 20 may have a shape of circle (FIG. 3A), square (FIG. 3B), triangle (FIG. 3C), or another suitable shape from a top-view. The plasmon resonance wavelength $\lambda_{LSP}$ of the periodically arranged nano structures 20 is between $0.85 n_s \times P$ to $1.15 n_s \times P$, where $n_s$ is the refractive index of the substrate. If the plasmon resonance wavelength $\lambda_{LSP}$ is beyond the above range, the resonance spectrum will be widened to reduce the spectra resolution of the sensing chip.

Figure 1D:
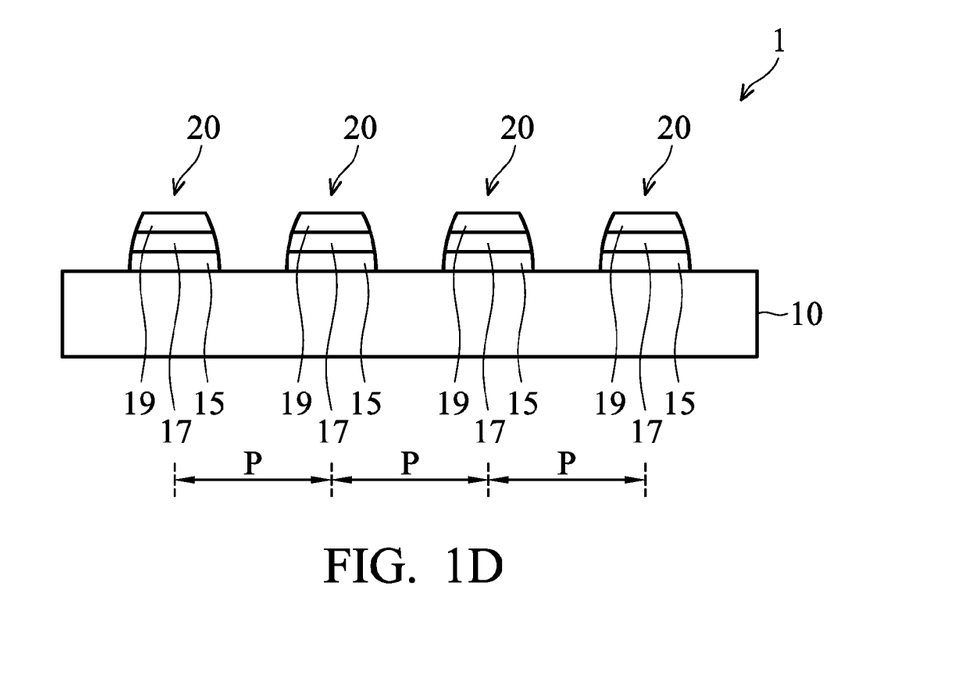

As shown in FIG. 1D, the area of the bottom metal layer 15 is greater than the area of the top metal layer 19. In one embodiment, the bottom metal layer 15 has a width of 50 nm to 1000 nm. A bottom metal layer 15 with an overly large width makes the plasmon resonance wavelength red-shift to the IR range, thereby increasing the cost of related spectroscopic equipment. A bottom metal layer 15 with an overly small width makes it hard to control the uniformity of the size of the nano structure. In one embodiment, the middle dielectric layer 17 has a width of 40 nm to 800 nm. A middle dielectric layer 17 with an overly large or small width make the nano structure is not easily manufactured. In one embodiment, the top metal layer 19 has a width of 10 nm to 700 nm. A top metal layer 19 with an overly large width make the plasmon resonance wavelength red-shift to the IR range, thereby increasing the cost of related spectroscopic equipment. A top metal layer 19 with an overly small width makes it hard to control the uniformity of the size of the nano structure.

Figure 1E:
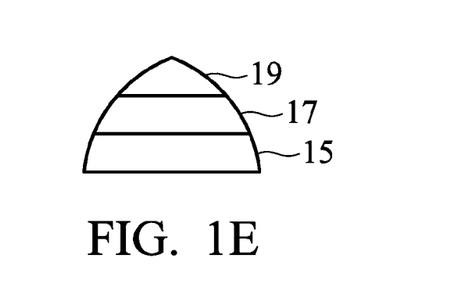
FIGS. 1E to 1G show cross-sectional views of the nano structure units in embodiments of the disclosure.
Figure 1F:
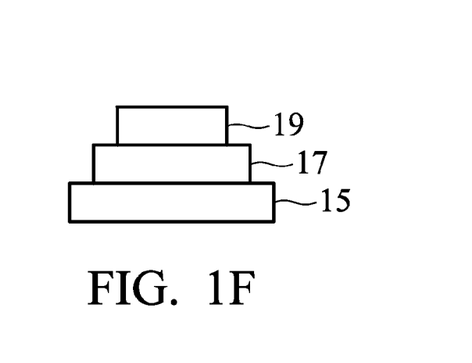
Figure 1G:
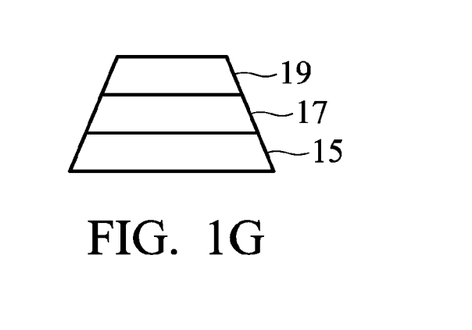

Although the nano structures 20 in FIG. 1D have a cone-like cross-sectional shape, they may have other cross-sectional shapes, such as a hill, as shown in FIG. 1E, a stair, as shown in FIG. 1F, or the like. It should be understood that the nano structures 20 in the drawings have curved sidewalls, but they may have straight sidewalls as shown in FIG. 1G. In one embodiment, the top of the nano structures 20 can be a curved round other than a plane.

Figure 4:
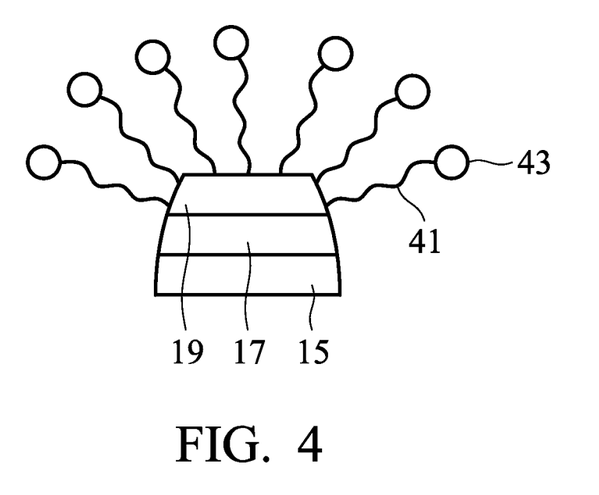
FIG. 4 shows an analyte connected to a top metal layer of the nano structure through a surface modification linker in embodiments of the disclosure.

The sensing chip 1 can be directly put into a medium (such as water or air) containing the analyte, thereby fixing the analyte on the nano structures 20 through the interaction (such as van der Waal's force or physical adsorption) between the surface of the nano structures 20 and the analyte. The peak shift between the absorption spectra of the chip in different media is then measured to quantify the effective refractive index of the analyte for calculating the concentration of the analyte. In one embodiment, a linker 41 can be further bonded onto the surface of the top metal layer 19, so that the analyte is connected to the surface of the top metal layer 19 through the linker 41, as shown in FIG. 4. The type of the linker 41 is related to the types of the top metal layer 19 and the analyte 43. For example, when the top metal layer 19 is gold and the analyte is an antibody, the linker can be a small molecule with a terminal group of thiol and another terminal group of carboxyl or amine, such as cysteamine, 11-mercaptoundecanoic acid (11-MUA), 11-Amino-1-undecanethiol hydrochloride), or the like.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Example 1

Figure 5A:
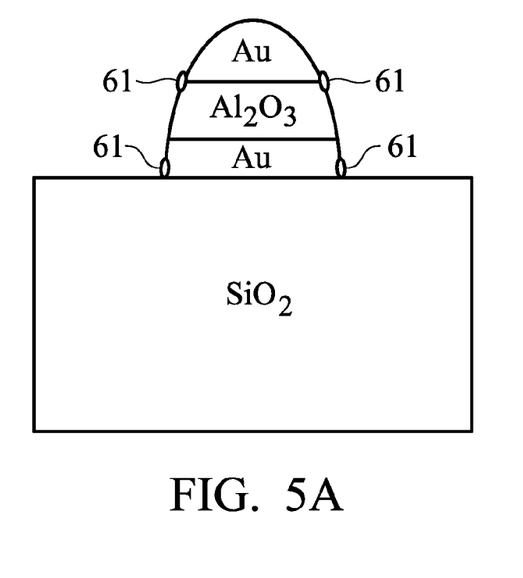
FIGS. 5A and 5B show cross-sectional views of the nano structure units in embodiments of the disclosure and prior art respectively.
Figure 5B:
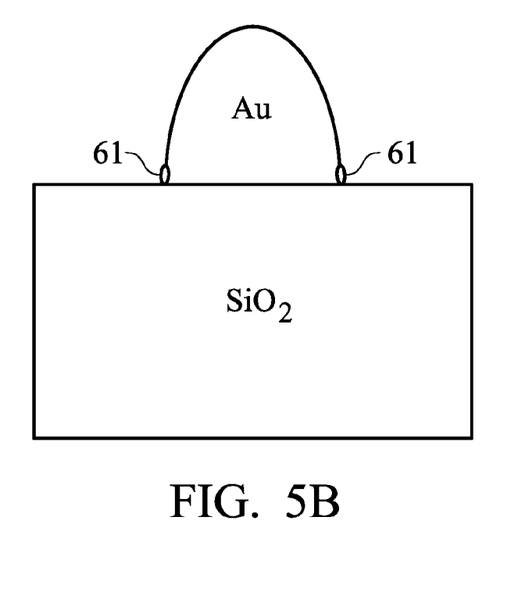

An MIM nano structure of gold/alumina/gold was formed on a silica substrate as shown in FIG. 5A, a nano structure of a single layered gold was formed on another silica substrate as shown in FIG. 5B, and distributions of hot spots 61 of the nano structures were compared. In FIG. 5A, the nano structure has a bottom metal layer (gold) thickness of 10 nm, a middle dielectric layer (alumina) thickness of 20 nm, and a top metal layer (gold) thickness of 40 nm. The nano structure in FIG. 5A had a width of 200 nm, and a plurality of the nano structures in FIG. 5A were arranged in an arrange period of 650 nm. In FIG. 5B, the single layered gold of the nano structure had a thickness of 70 nm. The nano structure in FIG. 5B had a width of 200 nm, and a plurality of the nano structures in FIG. 5B were arranged in an arrange period of 650 nm.

The hot spots of the single layered metal nano structure in FIG. 5B were mainly located at sharp ends of the joints between the silica substrate and the gold nano structure. The hot spots of the MIM nano structure in FIG. 5A were not only located at sharp ends of the joints between the silica substrate and the nano structure. In addition, other hot spots with a higher strength were located at sharp ends of the joint between the top metal layer (gold) and the middle dielectric layer (alumina) of the nano structure in FIG. 5A.

Figure 6A:
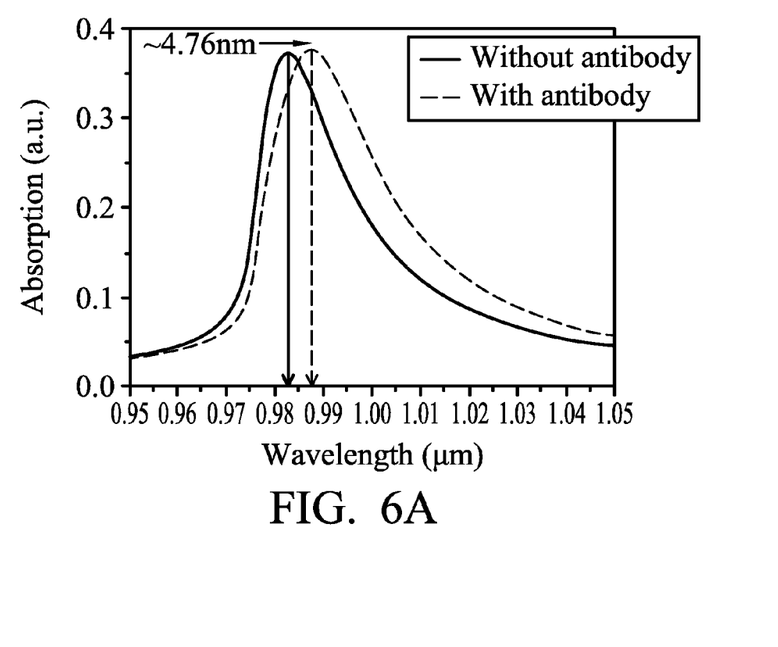
FIGS. 6A and 6B show spectra of simulation of the analyte on the nano structure in embodiments of the disclosure.
Figure 6B:
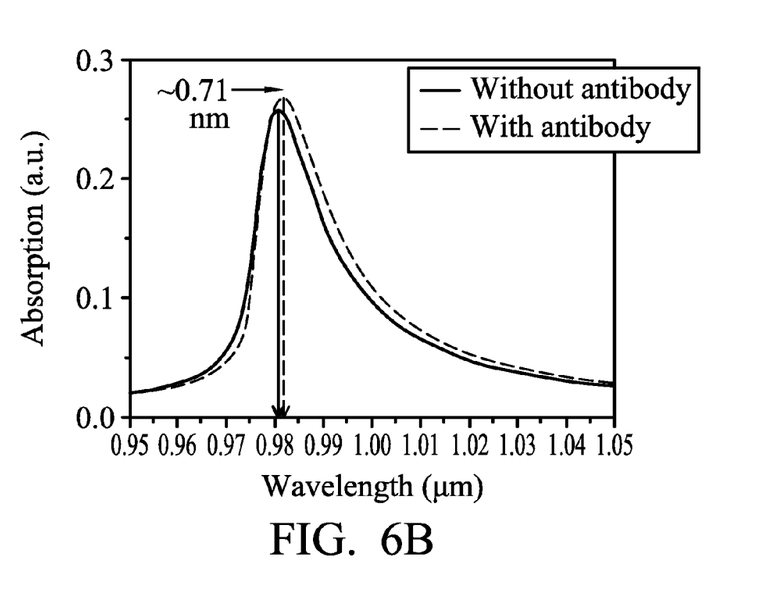

Character spectra of an analyte connected on the nano structures were simulated by a finite difference time domain (FDTD) method. The refractive index of a buffer solution (medium) was set as 1.33, the refractive index of the analyte (antibody) was set as 1.5, and the analyte was uniformly disposed on surfaces of the nano structures as a layer with a thickness of 20 nm, and the spectra of simulation are shown in FIGS. 6A and 6B. As shown in comparison of FIGS. 6A and 6B, The MIM nano structure efficiently enhanced the sensitivity of the chip, e.g. 6.7 times the sensitivity of the chip having the nano structures with single layered of gold.

The analyte distribution influenced by the MIM nano structures is further analyzed. About 75% of spectra change came from the analyte conjugated on an upper portion of the nano structure. In contrast, only 20% of spectra change came from the analyte conjugated on a lower portion of the nano structure. The antibody in the liquid medium follow Brownian motion which means they randomly collides with the nano structure during the antibody conjugation process. In practice, and the antibody conjugated on the upper portion of the nano structure might block the antibody to be close the lower portion of the nano structure due to the steric effect. As such, adjusting the hot spots' location to the upper portion of the nano structure (e.g. between the top metal layer and the middle dielectric layer) might efficiently increase the chance of the analyte attaching at the hot spots, thereby improving the detection limit of the analyte. Accordingly, even if the MIM nano structures and the single layered metal nano structures had similar distribution density and size, the MIM nano structure would have a higher detection sensitivity and detection limit than that of the single layered metal nano structure.

Example 2

Figure 7A:
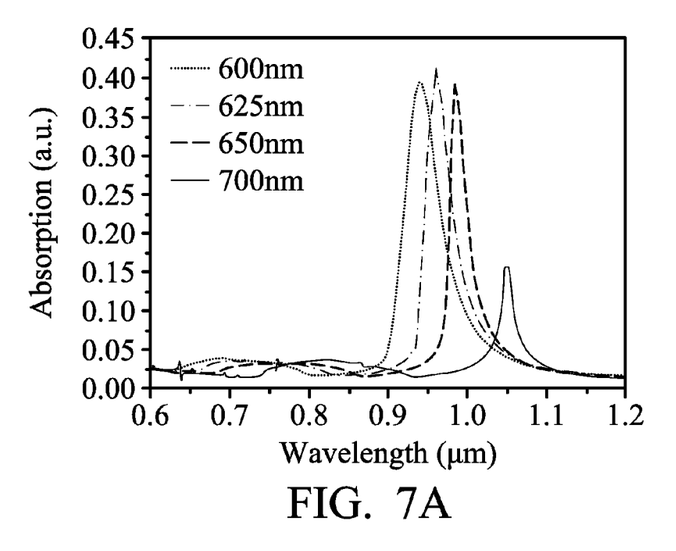
FIGS. 7A and 7B show characteristics of localized surface plasmon resonance spectra of the nano structure in embodiments of the disclosure by simulations.
Figure 7B:
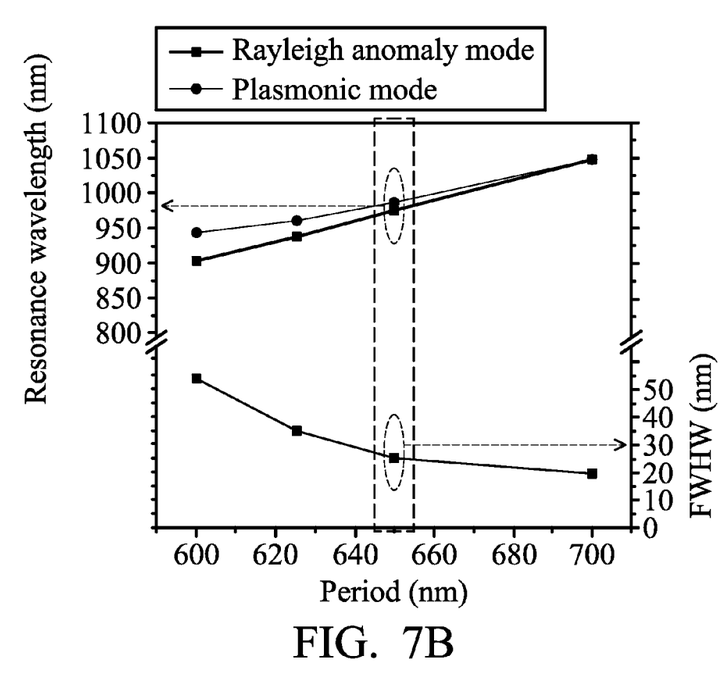

The MIM nano structures in Example 1 were selected to adjust their arrange period, and plasmon resonance spectra thereof was simulated as shown in FIG. 7A. As shown in the simulation results, the larger period P made the resonance peak have a smaller FWHW due to the coupling of the close LSPR mode of the structural element and the Rayleigh anomaly mode from the diffraction of the periodically arranged nano structures, as shown in FIG. 7B. As shown in FIG. 7B, the suitable arrange period for the nano structures should be about 650 nm.

Example 3

Figure 8:
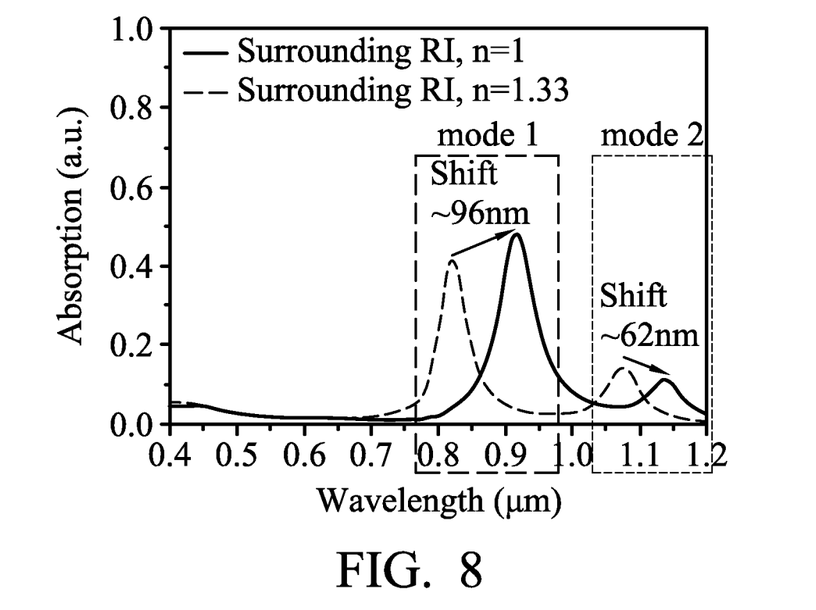
FIG. 8 shows the spectra change of the same nano structure in different surrounding media of embodiments in the disclosure, which indicate mode 1 is more sensitive than mode 2.
Figure 9:
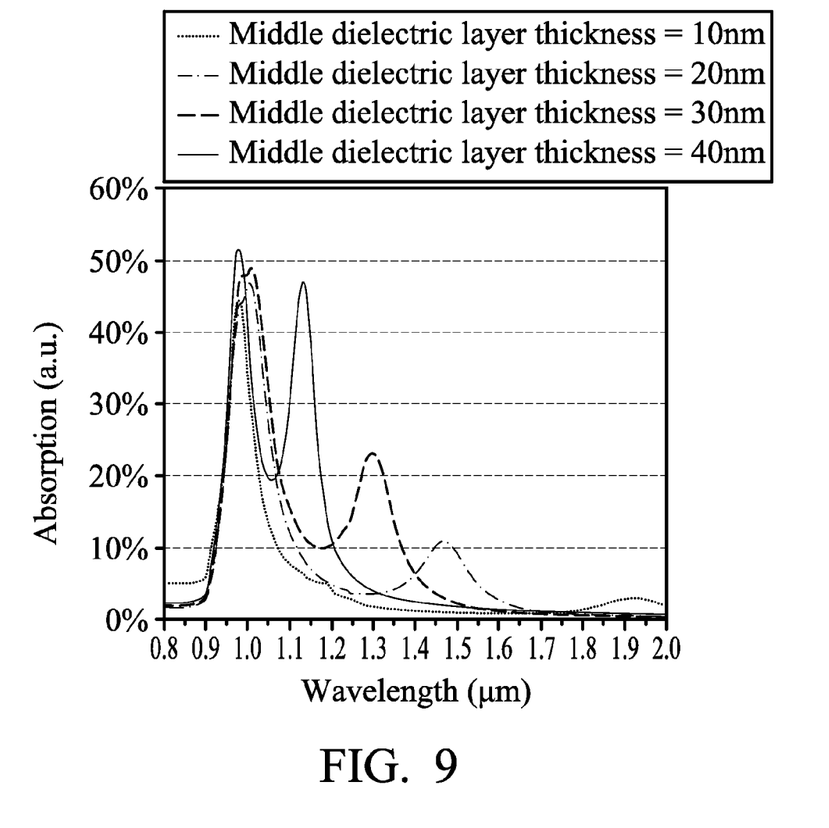
FIG. 9 shows the spectra change of the nano structures with middle dielectric layers of different thicknesses in the same medium of embodiments of the disclosure.

The spectra change of the nano structures in two surroundings, air (n=1) and water (n-1.33), is shown in FIG. 8. The spectra have two character peaks such as mode 1 and mode 2. Mode 1 is more sensitive to the refractive index change of the surroundings than mode 2. In FIG. 9, the top metal layer thickness (15 nm) and the bottom metal layer thickness (15 nm) in different nano structures were fixed, and only the middle dielectric layer thicknesses in the different nano structures were verified to determine the influence of the middle dielectric layer thickness in the character spectra. As shown in a result of simulation, the thicker middle dielectric layer make two character spectra be closer and even overlap. On the other hand, the thinner middle dielectric layer make two character spectra be separated due to strong surface plasmon coupling of the top and bottom metal layers. Because the detection only utilized mode 1, the middle dielectric thickness should not be overly large (e.g. less than 10 nm) to avoid the interference of mode 2. In other words, the overlap of mode 1 and mode 2 may interfere with the character spectra location and reduce the sensor dynamic range, which should be prevented.

Example 4

Figure 10A:
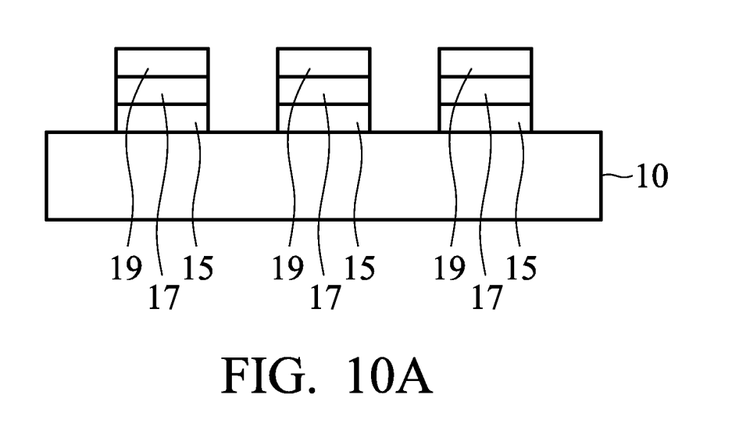
FIGS. 10A and 10B show cross-sectional views of the nano structures in embodiments of the disclosure.
Figure 10B:
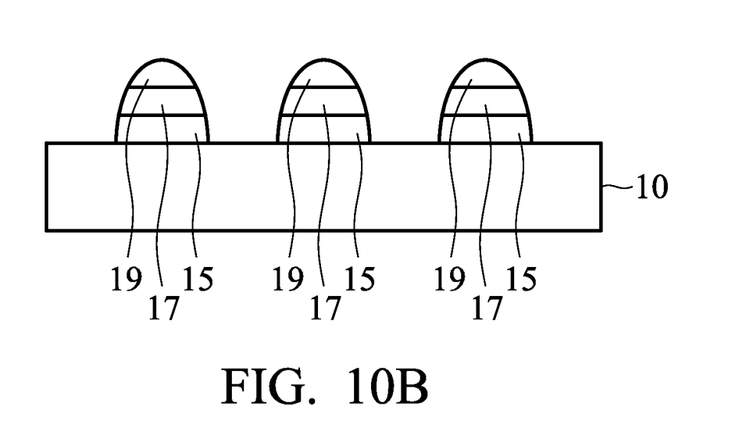

MIM nano structures of gold/alumina/gold were formed on a silica substrate as shown in FIG. 10A, and other MIM nano structures of gold/alumina/gold were formed on another silica substrate as shown in FIG. 10B. The bottom metal layers (gold) of both of the nano structures had the same thickness of 10 nm, the middle dielectric layers (alumina) of both of the nano structures had the same thickness of 25 nm, and the top metal layers (gold) of both of the nano structures had the same thickness of 10 nm. Both of the nano structures in FIGS. 10A and 10B had the same width of 200 nm and the same arrange period of 600 nm. As shown in FIGS. 10A and 10B, the difference between the MIM nano structures was the cross-sectional views thereof. In FIG. 10A, the nano structures had a cross-sectional view of a semi-elliptical shape, in which the area of the top metal layer with a width of 140 nm was less than the area of the bottom metal layer with a width of 200 nm. In FIG. 10B, the nano structures had a cross-sectional view of a rectangular shape, in which the top metal layer and the bottom metal layer had the same area. The sensitivities of the chips to the change of different refractive indexes can be obtained by calculating the resonance wavelengths in different surroundings with the different refractive indexes. As a result, the sensitivity of the chip with the nano structures in FIG. 10B (299 nm/RIU) was 7% higher than the sensitivity of the chip with the nano structures in FIG. 10A (269 nm/RIU). A comparison of the properties of the nano structures is tabulated in Table 1.

TABLE 1

| Structure | Resonance peak in air | Resonance peak in water | Sensitivity (nm/RIU) |
|---|---|---|---|
| FIG. 10A | 833 nm | 923 nm | 269 |
| FIG. 10B | 825 nm | 921 nm | 299 |

As shown in Table 1, the nano structures with a bottom metal layer area that is larger than the top metal layer area had a higher sensitivity.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A sensing chip, comprising:
a substrate; and a plurality of nano structures periodically arranged on the substrate,
wherein:
each of the nano structures includes a bottom metal layer disposed on the substrate, a middle dielectric layer disposed on the bottom metal layer, and a top metal layer disposed on the middle dielectric layer,
the bottom metal layer has an area that is larger than that of the top metal layer,
the bottom metal layers of the different nano structures are separated from each other,
the middle dielectric layers of the different nano structures are separated from each other,
the top metal layers of the different nano structures are separated from each other, and
the bottom metal layer has a width of 50 nm to 1000 nm, the middle dielectric layer has a width of 40 nm to 800 nm, and the top metal layer has a width of 10 nm to 700 nm.

2. The sensing chip as claimed in claim 1, wherein the nano structures have a plasmon resonance wavelength $\lambda_{LSP}$ and an arrange period P, the substrate has a refractive index $n_s$, the arrange period P being a range of 100 nm to 2000 nm, the refractive index $n_s$ being a range of 1.2 to 4.5, and the plasmon resonance wavelength $\lambda_{LSP}$ being a range of 0.85 $n_s \times P$ to 1.15 $n_s \times P$.

3. The sensing chip as claimed in claim 1, wherein the substrate comprises a dielectric material.

4. The sensing chip as claimed in claim 1, wherein the nano structures are periodically arranged in a rectangular manner or in a hexagonal manner.

5. The sensing chip as claimed in claim 1, wherein the nano structures have a top-view shape of a circle, square, or triangle.

6. The sensing chip as claimed in claim 1, wherein the nano structures have a cross-sectional shape of a cone, hill, or stair.

7. The sensing chip as claimed in claim 1, wherein the nano structures have a width of 50 nm to 1000 nm.

8. The sensing chip as claimed in claim 1, wherein the nano structures have a width and a height, and the width is greater than or equal to the height.

9. The sensing chip as claimed in claim 1, wherein the middle dielectric layer comprises alumina, silica, silicon nitride, or a combination thereof.

10. The sensing chip as claimed in claim 1, wherein each of the top metal layer and the bottom metal layer independently comprises gold, silver, aluminum, chromium, copper, titanium, or an alloy thereof.

11. The sensing chip as claimed in claim 1, wherein the top metal layer has a thickness of 1 nm to 50 nm.

12. The sensing chip as claimed in claim 1, wherein the middle dielectric layer has a thickness of 1 nm to 10 nm.

13. The sensing chip as claimed in claim 1, wherein the bottom metal layer has a thickness of 1 nm to 50 nm.

14. The sensing chip as claimed in claim 1, further comprising a linker bonded to a surface of the top metal layer to connect an analyte to the surface of the top metal layer through the linker.

* * * * *